United States Patent [19]
Scherer et al.

[11] Patent Number: 5,824,468
[45] Date of Patent: Oct. 20, 1998

[54] DETECTION OF LISTERIA BY MEANS OF RECOMBINANT BACTERIOPHAGES

[75] Inventors: Siegfried Scherer; Martin Loessner, both of Friesing, Germany

[73] Assignee: Merck Patent Gesellschaft mit beschrankkter Haftung, Darmstadt, Germany

[21] Appl. No.: 648,978

[22] Filed: May 17, 1996

[30] Foreign Application Priority Data

May 18, 1995 [DE] Germany .................. 195 17 940.4

[51] Int. Cl.$^6$ .............. C12Q 1/70; C12Q 1/04; C12N 15/00; C12N 15/64
[52] U.S. Cl. .............. 435/5; 435/172.3; 435/320.1; 435/8; 435/29; 435/34
[58] Field of Search .................. 435/320.1, 29, 435/172.3, 34, 5, 8

[56] References Cited

U.S. PATENT DOCUMENTS 5,498,525  3/1996  Rees et al. ........................... 435/29

FOREIGN PATENT DOCUMENTS

WO 90/04041  4/1990  WIPO .
WO 93/16172  8/1993  WIPO .

OTHER PUBLICATIONS

Loessner et al., J. Gen. Virol. 75:701–710 (1994).
Köhler, et al., Infection and Immunity, vol. 58, No. 6, pp. 1943–1950 (Jun. 1990).
Datta, et al., Applied and Environmental Microbiology, vol. 54, No. 12, pp. 2933–2937 (Dec. 1988).
Deneer, et al., Applied and Environmental Microbiology, vol. 57, No. 2, pp. 606–609, (Feb. 1991).
Border, et al., Letters in Applied Microbiology, vol. 11, pp. 158–162 (1990).
Furrer, et al., Journal of Applied Bacteriology, vol. 70, pp. 373–379 (1991).
Lerner, Adv in Immunol., vol. 36, pp. 1–44 (1984).

*Primary Examiner*—George C. Elliott
*Assistant Examiner*—Johnny F. Railey, II
*Attorney, Agent, or Firm*—Millen, White, Zelano, & Branigan, P.C.

[57] ABSTRACT

The invention relates to a detection procedure for bacteria of the genus Listeria, comprising the steps:

(a) provision of a DNA vector prepared by means of recombination techniques, comprising a genetic system comprising DNA which encodes the expression of one or more proteins, the proteins not being a gene product of bacteria of the genus Listeria and it being possible to determine the presence of the proteins by a detection reaction, and the DNA vector infecting the bacteria of the genus Listeria and it being possible in this way to transfer the genetic system to the bacteria;

(b) mixing of the sample with said DNA vector under conditions which allow an infection of bacteria of the genus Listeria by the DNA vector;

(c) expression of the detectable proteins in the bacteria of the genus Listeria;

(d) detection of the detectable proteins, the presence of bacteria of the genus Listeria being detected, and to recombinant DNA vectors and reagent compositions suitable for this detection procedure.

12 Claims, 2 Drawing Sheets

DETECTION OF LISTERIA BY MEANS OF RECOMBINANT BACTERIOPHAGES

BACKGROUND OF THE INVENTION

The invention relates to a detection procedure for bacteria of the genus Listeria, and to reagents suitable for this detection procedure.

The members of the genus Listeria are gram-positive rod-like bacteria which occur ubiquitously. The species *L. monocytogenes* is pathogenic to man.

The cause of infections with listeria is often contaminated foodstuffs, in which the bacteria can multiply even at low temperatures of around 4° C. Various listeria epidemics were thus traced back to the consumption of contaminated foods, e.g. untreated milk, cheese or coleslaw. Rapid detection procedures for the detection of listeria, in particular in foodstuffs or clinical samples, are thus urgently necessary.

The detection of listeria is carried out in a known manner by means of procedures based on the culture of the microorganisms. The procedure described in Int. J. Food Microbiol. 4 (1987), 249–256 takes two weeks. A somewhat more rapid procedure is recommended by the International Dairy Foundation (IDF); however it takes at least 6–8 days. Because of their length, both procedures are unsuitable for a rapid identification. Both procedures are moreover labor-intensive, as for the production of individual colonies nutrient media have to be inoculated several times, and as the isolates then have to be characterized by means of biochemical and serological investigation methods.

A prerequisite for the use of immunological tests is that the antigen is expressed, which is not the case for all proteins at any time. The tests admittedly last only a few hours, but in these procedures a two-day pre-enrichment culture is needed, as the detection limit is $10–1000 \times 10^3$ cells. DNA probes have a detection limit of the same order of magnitude. A prior multiplication of the bacteria is therefore also necessary for these procedures: foodstuff samples or dilutions thereof are streaked out on agar plates, and the inoculated plates are incubated and then investigated in the colony hybridization procedure using a radio-labelled DNA probe. Detection is carried out by autoradiography. This method too is moreover labor and time-consuming.

The polymerase chain reaction (PCR) allows the in vitro replication of nucleic acids; a preculture is in general not necessary in this procedure. The detection limit is $0.5 \times 10^3$ cells. As, however, DNA from dead cells or alternatively isolated DNA is also replicated in this procedure, contamination with dead cells cannot be differentiated from contamination with living cells.

The limitations of these methods indicate the need to provide improved agents and methods for the detection of bacteria of the genus Listeria.

EP 0 168 933 (U.S. Pat. No. 4,861,709) discloses a detection procedure for bacteria, e.g., *Escherichia coli*, based on the use of a recombinant bacteriophage. This phage contains the lux gene from Vibrio fischeri and thus makes possible the detection of *E. coli* by bioluminescence with a good detection limit ($0.5 \times 10^3$ cells). Using temperate phages, G. J. Sarkis et al. (1995) Molecular Microbiology 15, 1055–1067 describe a detection procedure for mycobacteria. In these detection procedures, only metabolically active bacterial cells are detected; interference due to dead bacterial cells as in the PCR technique does not occur.

SUMMARY OF THE INVENTION

The invention provides procedures for the detection of bacteria of the genus Listeria in a sample, comprising the steps:

(a) provision of a DNA vector prepared by means of recombination techniques, comprising a genetic system comprising DNA which encodes the expression of one or more proteins, the proteins not being a gene product of bacteria of the genus Listeria and it being possible to determine the presence of the proteins by a detection reaction, and the DNA vector infecting the bacteria of the genus Listeria and it being possible in this way to transfer the genetic system to the bacteria;

(b) mixing of the sample with said DNA vector under conditions which allow an infection of bacteria of the genus Listeria by the DNA vector;

(c) expression of the detectable proteins in the bacteria of the genus Listeria;

(d) detection of the detectable proteins, the presence of bacteria of the genus Listeria being detected.

The preferred DNA vector is a recombinant bacteriophage from the myoviruses group having the morphotype A1. In a particularly preferred embodiment, this recombinant bacteriophage contains a gene which codes for a luciferase from bacteria, the expression of the luciferase being detected by light emission.

The invention further provides a recombinant Listeria bacteriophage from the myoviruses group having the morphotype A1, whose genome contains in integrated form a gene which encodes a luciferase from bacteria.

The invention also provides reagent compositions comprising, in addition to a growth medium for bacteria of the genus Listeria, infectious Listeria bacterio-phages from the myoviruses group having the morphotype A1, whose genome contains in integrated form a gene which encodes a luciferase from bacteria.

BRIEF DESCRIPTION OF THE DRAWINGS

Various other objects, features and attendant advantages of the present invention will be more fully appreciated as the same becomes better understood when considered in conjunction with the accompanying drawings, wherein.

L.mono is *L. monocytogenes*

L.ivan is *L. ivanovii*

L. seel is *L. seeligeri*

Figure 1:
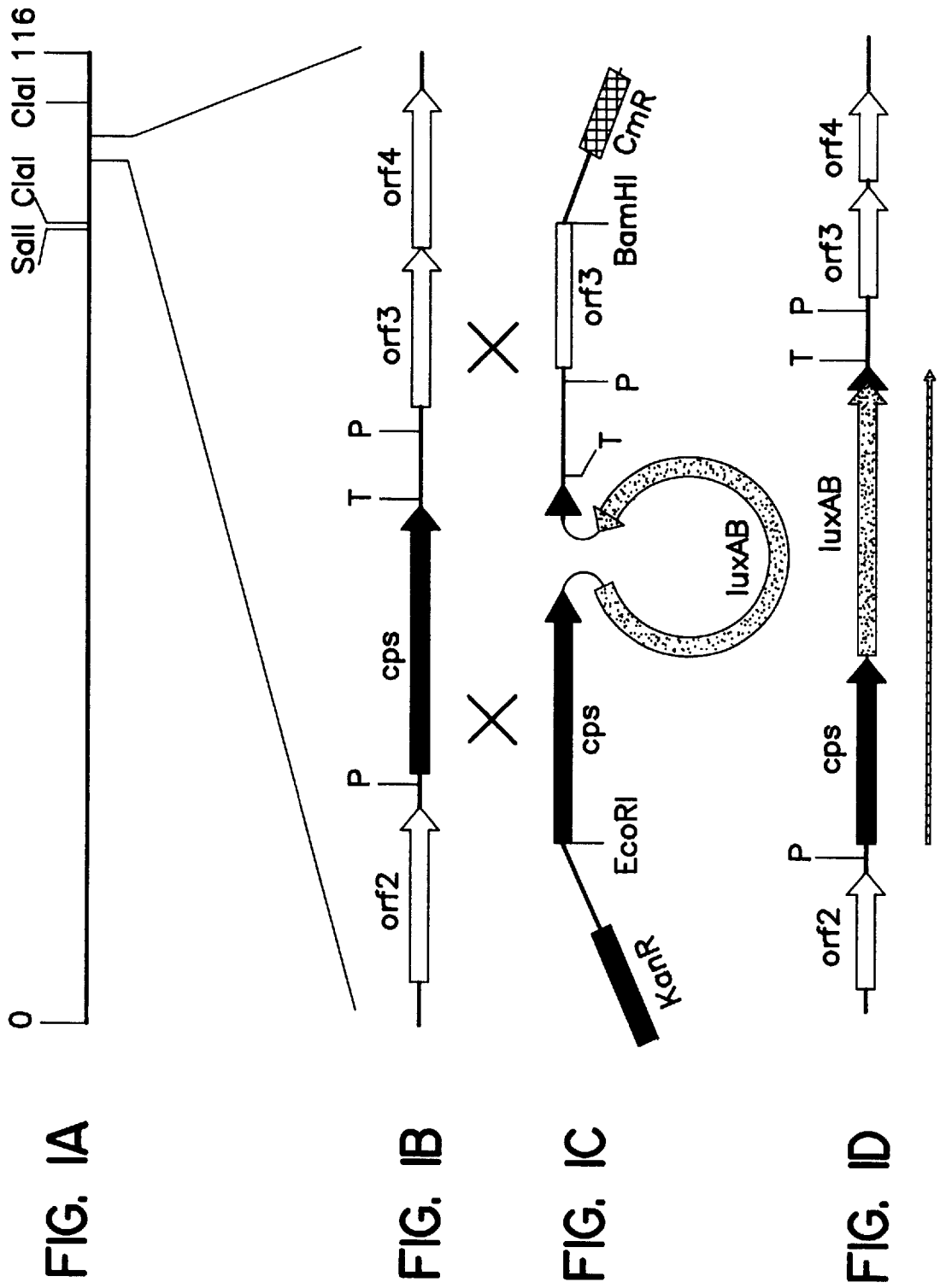
FIG. 1 (A–D) Part A shows a general view of the genome of the Listeria bacteriophage A511 (wild-type). Part B shows a section of this gene map. Part C shows the insertion of the gene luxAB into the genome of the wild-type phage. Part D shows the resulting transcript. The symbols P and T mark promoter or terminator sequences; cleavage sites and genes are marked using the customary abbreviations.

The grey crosshatching from 0 to about 50 RLU (relative light unit) marks the background of the measurement signal.

The invention will be described in greater detail below.

By "vector" is meant a nucleic acid molecule that is capable of self-replication when introduced into a suitable host cell. In general, the vectors used as starting materials for the recombinant vectors of the present invention are bacteriophages which are highly specific, and preferably absolutely specific, for infecting bacteria of the genus Listeria, and wherein the recombinant vectors retain that specificity. For example, a suitable vector is the Listeria bacteriophage A511, deposited in the Reference Centre for Bacterial Viruses, Felix d'Herelle; Laval University, Quebec, Canada specifically lyses bacteria of the genus Listeria (inevitably lytic). It is a myovirus (A1 morphotype) of complex construction. With respect to essential features, the Listeria phage A511 differs from other known Listeria phages; the differences relate to morphology, host range, protein profiles (electrophoresis in SDS gel, isoelectric focusing, amino acid composition of the main structural proteins, DNA/DNA hybridization). The genome size of A511 is approximately 116 kbp.

For detection of the presence of bacteria of the genus Listeria, marker genes are employed. These are genes which can be detected upon infection by the vector of a suitable host cell and subsequent culturing of the cells under conditions suitable for expression of the marker genes. It is preferred that the marker genes are those which do not occur in the bacteria of the genus Listeria, and which are inserted into the vector, e.g., the phage A511, using recombinant techniques. Such genes and their gene products are known; they include the lux gene which occurs in variants in various luminescent bacteria, for example of the genus Vibrio. The incorporation of the lux gene allows detection by luminescence measurement. The gene luxAB from *Vibrio harveyi* is preferably used.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

In the foregoing and in the following examples, all temperatures are set forth uncorrected in degrees Celsius; and, unless otherwise indicated, all parts and percentages are by weight.

The entire disclosures of all applications, patents and publications, cited above and below, and of corresponding German application DE 195 17 940.4, filed May 18, 1995, are hereby incorporated by reference.

EXAMPLES

Example 1

In one embodiment of the invention, the lux gene was inserted into a strongly expressed gene range (region) of the Listeria phage A511. To do this, the main proteins of capsid and tail sheath were identified by transferring the proteins from SDS gels to carrier membranes (Western blot). The determination of the N-terminal amino acid sequences made possible the preparation of specific oligonucleotides with whose aid (Southern hybridization) it was possible to identify corresponding A511 DNA fragments with the genes for the proteins sought. After subcloning (in *E. coli* K-12) and nucleotide sequencing of a total of 4 different fragments, a continuous sequence of 10152 bp resulted which, in addition to nine other open reading frames, contains the genes for the main capsid protein (cps) and for the tail sheath protein (tsh). Above cps is located a strong, so-called "late" promoter, which is selectively activated in the course of the expression of the phage genes, and leads to a very high copy number of the corresponding mRNA transcripts. 50 bp before the 3'-end of cps (stop codon), is a single cleavage site for SnaBI. A "blunt"0 cut end can thus be produced at this site. Below the gene (approximately 50 bp distance) is located an effective transcription terminator.

For the construction of the recombinant virus A511::luxAB according to the invention, a fusion product of the luciferase genes (luxAB, about 2.1 kbp) from *Vibrio harveyi* having suitable translation signals (ribosome binding site, intermediate region, start codon) was first prepared and inserted into the genome of the phage A511 directly below cps and before the terminator. The following individual steps were carried out according to known methods:

Subcloning (in *E. coli*) of a 2123 bp SspI fragment (F3s) of A511 (the SnaBI cleavage site is central) into the SmaI cleavage site of pBluescriptII yields pBS511-F3s.

Amplification of luxAB (present on promoter-test plasmid pSP331) using specific primers. The 5'-primer (104 mer) contains the 50 nucleotides of SnaBI cleavage site in cps to stop codon, optimized ribosome binding site, start codon and 35 nucleotides from the 5'-end of luxAB. The 3'-primer (39 mer) contains (complementary) stop codon and 25 nucleotides from the 3'-end of luxAB. Primary amplification in the PCR by means of Taq polymerase; addition of Pfu polymerase before the last cycle yields an increased proportion of products having blunt ends.

Insertion of the modified luxAB fragment into SnaBI-cleaved pBS511-F3s yields pBS511-F3s-luxAB. Checking of the correct orientation (restriction digestion) and integrity of the 3'-end of cps (DNA sequencing).

Excision of the F3s-flanked luxAB cassette with BamHI and EcoRI (present in MCS from pBluescript II).

Insertion of the cassette into the *E. coli*-Listeria shuttle vector pCK 1 opened with BamHI/EcoRI and transformation in *E. coli* W3110 yields pCK511-F3s-luxAB.

Isolation and purification of the plasmid; checking correct structure and orientation.

Electrotransformation of pCKS511-F3s-luxAB in *Listeria monocytogenes* WSLC 1001 and *Listeria ivanovii* WSLC 3009 (Gene-Pulser®, BioRad).

Infection of 1001(pCKS 11-F3s-luxAB) and 3009 (pCKS511-F3s-luxAB) with A511 (wild-type). By homologous recombination between the luxAB-flanking A511 fragments (F3s) and A511 DNA formed during infection in the cell, there is integration (double crossover) of luxAB into the A511 genome (frequency about $5 \times 10^{-4}$) (see FIG. 1).

Enrichment of recombinant phages in lysates of 3009 (pCK511-F3s-luxAB) by means of a dilution method in which 20 batches each containing $5 \times 10^3$ phages are first separately replicated. Positive batches can be recognized by means of the luxAB expression after infection of 1001 or 3009 host cells. Repetition of this procedure several times with appropriately selected dilutions (up to the single plaque) makes possible isolation of A511::luxAB.

Replication of A511::luxAB on host strain WSLC 3009; washing and concentration of the phage particles by tangential-flow filtration (removal of the endolysin formed during morphogenesis and of luciferase AB) (Cross-Sart® membranes, Sartorius, Germany); concentration adjustment to about 1010 plaque-forming units/ml.

Isolation and restriction analysis of AS511::luxAB DNA, to confirm the correct integration of luxAB (double crossover instead of single crossover with integration of the entire plasmid).

The experimental conditions for the expression of luxAB after phage infection were determined.

The expression parameters were optimized using cultures of various listeria strains (*L. monocytogenes* WSLC 1001 (Serovar 1/2c), ScottA (4b), *L. ivanovii* WSLC 3009):

Medium for infection: brain-heart broth (half-concentrated) (Oxoid, UK);

Apply Listeria cells in log-phase (preincubation at 30°–35° C.) dilutions (about $10^7$ cells/ml).

1 ml of cell suspension plus 30 μl of phage suspension (=about $3\times10^8$ phages/ml)

Incubation temperature: 18°–20° C. (luciferase is temperature-sensitive)

Measurement in a tube luminometer (LB9501, Berthold)

Injection of 50 μl of 0.25% nonanal (nonyl-aldehyde, Aldrich), measurement and integration of the RLUs for 5 s.

Best measurement point (maximum light emission, measured in RLUs (Relative Light Units)): about 120–130 min. post-infection (at 20° C.)

Cultures of various Listeria strains (*L. monocytogenes* WSLC 1001 (Serovar 1/2c), WSLC 1040 (1/2a), WSLC 1066(1/2b), ScottA (4b), *L. ivanovii* WSLC 3009 (5), *L. seeligeri* WSLC 4007 (1/2b) were used in order to determine the detection limit; the procedure in this case was as follows:

Apply dilutions ($10^2$, $5\times10^2$, $10^{3}$, $2.5\times10^3$, $5\times10^3$, $10^4$ cells/ml)

Controls:
A) Without A511::luxAB (zero control)
B) Without cells, without A511::luxAB (background control)

Figure 2:
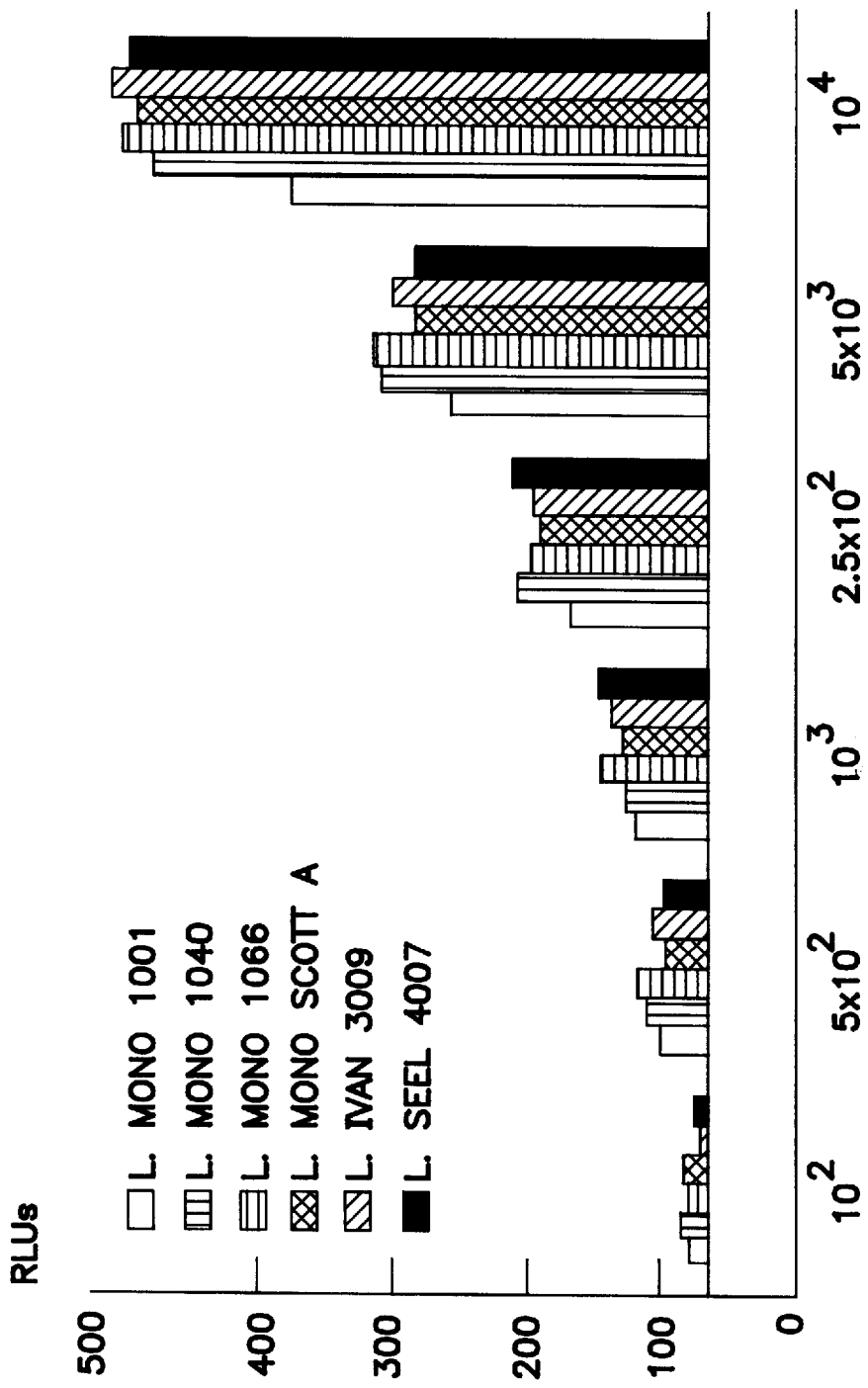
FIG. 2 shows the detection limits for various strains of listeria; in these.

Infection according to optimum parameters (see above), measurement of the RLUs (see FIG. 2)

Detection limit at about $5\times10^2$ cells; reliable positive limit at about $10^3$ cells.

Example 2

In a further experiment, the detection of listeria in a foodstuff sample was investigated; to do this the procedure was as follows:

Artificial contamination of lettuce leaves (iceberg lettuce) with 0 (=control); 0.1; 1.0 and 10 cells of *L. monocytogenes* ScottA/g of lettuce.

Storage at 4° C. for 1 and 7 days.

Mixing of 25 g each of lettuce with 225 ml of ANC broth or Listeria selective broth.

Incubation at 30° C., for 24 hours.

Brief secondary enrichment (non-selective): 1 ml of primary enrichment plus 5 ml of brain-heart broth (half-concentrated); incubation for 3–4 hours at 30°–35° C.

Infection of 1 ml of test culture according to optimum parameters (see above); measurement of the RLUs.

Result: The batch containing 0.1 cells of *L. monocytogenes* ScottA per gram of lettuce gives a clearly positive signal after storage of the lettuce for 1 and 7 days.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. An infectious recombinant bateriophage derived from a myophage of morphotype A1, species A511, comprising a marker gene exogenous to bacteria of the genus Listeria, wherein said gene encodes a marker gene product.

2. A bacteriophage of claim 1, where the gene product is luciferase.

3. A regent composition comprising a bacteriophage of claim 1 and growth medium for bacteria of the genus Listeria.

4. A reagent composition comprising a bacteriophage of claim 2 and growth medium for bacteria of the genus Listeria.

5. A method for the detection of bacteria of the genus Listeria in a sample, comprising:

a) mixing the sample with a reagent of claim 3 under conditions wherein said bacteriophage infects bacteria of the genus Listeria;

b) culturing the mixture of a) such that said marker gene is expressed in bacteria of the genus Listeria;

c) detecting the presence of the marker gene product in b), wherein expression of the marker gene product indicates the presence of bacteria of the genus Listeria in the sample.

6. A method of claim 5, wherein the marker gene product is an enzyme that catalyzes a reaction that produces a detectable reaction product.

7. A method of claim 6, wherein the detectable reaction product is detectable by light emission.

8. A method of claim 7, wherein the enzyme is luciferase.

9. A method of claim 5, wherein the marker gene product is a protein.

10. A method of claim 9, wherein the protein is detectable by immunoassay.

11. A method of claim 5, wherein the marker gene product is a nucleic acid.

12. A method of claim 11, wherein the nucleic acid is detectable by hybridization assay.

* * * * *